United States Patent [19]

Gesing et al.

[11] Patent Number: 4,895,850
[45] Date of Patent: Jan. 23, 1990

[54] INSECTICIDAL 1,2,3,4-TETRAHYDRO-5-NITRO-PYRIMIDINE DERIVATIVES

[75] Inventors: Ernst Gesing, Erkrath-Hochdahl; Hilmar Wolf, Langenfeld; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[21] Appl. No.: 271,555

[22] Filed: Nov. 15, 1988

[30] Foreign Application Priority Data

Nov. 18, 1987 [DE] Fed. Rep. of Germany ....... 3739264

[51] Int. Cl.[4] .................... C07D 487/04; A01N 43/90
[52] U.S. Cl. .................................. 514/258; 544/279; 544/280; 544/281
[58] Field of Search ............... 544/282, 279, 280, 281; 514/258

[56] References Cited

FOREIGN PATENT DOCUMENTS 3638121 12/1987 Fed. Rep. of Germany .

Primary Examiner—Mukund J. Shah
Assistant Examiner—C. L. Cseh
Attorney, Agent, or Firm—Sprung, Horn, Kramer & Woods

[57] ABSTRACT

Insecticidal 1,2,3,4-tetrahydro-5-nitro-pyrimidine derivatives of the formula

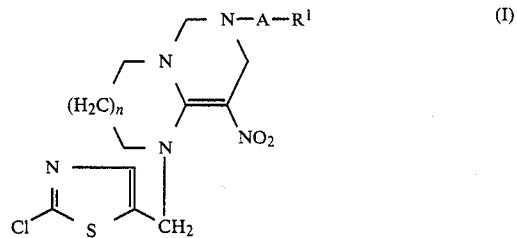

in which n is 0 or 1, A is a direct bond, $-(CH_2)_m-$ or $-(CH_2)_x-Y-(CH_2)_z$, m is a number from 1 to 4, x and z each independently is 0, 1 or 2, Y is oxygen, sulphur, —NH— or

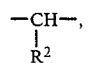

$R^2$ is optionally alkoxycarbonyl-substituted $C_1-C_4$-alkyl, or cyano, hydroxyl or phenyl, and $R^1$ is halogeno-$C_1-C_4$-alkyl or an optionally substituted radical from the group consisting of phenyl, naphthyl, anthryl, phenanthryl, pyridyl, furyl, thienyl, piperidyl and 1,3-benzodioxolyl, and their acid addition salts.

10 Claims, No Drawings

INSECTICIDAL 1,2,3,4-TETRAHYDRO-5-NITRO-PYRIMIDINE DERIVATIVES

The present invention relates to new 1,2,3,4-tetrahydro-5-nitro-pyrimidine derivatives, a process for their preparation and their use in pesticides, in particular as insecticides.

It is already known that certain pyrimidino-thiazines, such as, for example, 7-ethyl-9-nitro-3,4,7,8-tetrahydro-(2H,6H)-pyrimidino-[4,3-b]-1,3-thiazine, exhibit insecticidal properties (cf. U.S. patent specification No. 4,031,087).

The new 1,2,3,4-tetrahydro-5-nitro-pyrimidine derivatives of the formula (I)

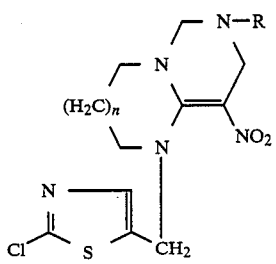
(I)

in which
n stands for the numbers 0 or 1
R stands for the —A—$R^1$ group
in which
A stands for a direct bond or for the —$(CH_2)_m$— or —$(CH_2)_x$—Y—$(CH_2)_z$ groupings,
where
m stands for the numbers 1 to 4,
x and z stand for the numbers 0, 1 or 2, it being possible for x and z to be identical or different,
Y stands for oxygen, sulphur or for the —NH— or

groupings,
where
$R^2$ stands for optionally alkoxycarbonyl-substituted $C_1$–$C_4$-alkyl, cyano, hydroxyl or for phenyl and
$R^1$ stands for halogeno-$C_1$–$C_4$-alkyl or for optionally substituted radicals from the series comprising phenyl, naphthyl, anthryl, phenanthryl, pyridyl, furyl, thienyl, piperidyl or 1,3-benzodioxolyl, and their acid addition salts have now been found.

Some of the new 1,2,3,4-tetrahydro-5-nitro-pyrimidine derivatives of the formula (I) possess an asymmetrically substituted carbon atom and can therefore be obtained in two optical isomer forms. The invention relates to both the isomer mixtures and the individual isomers.

Furthermore, it has been found that the 1,2,3,4-tetrahydro-5-nitro-pyrimidine derivatives of the formula (I) and their acid addition salts are obtained when nitromethylene derivatives of the formula (II)

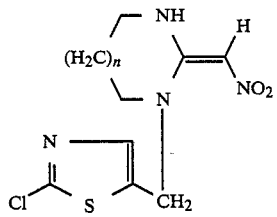

in which
n has the abovementioned meaning, are reacted with amines of the formula (III)

$$R^1—A—NH_2 \qquad (III)$$

in which
$R^1$ and A have the abovementioned meaning, in the presence of at least twice the molar amount of formaldehyde, if appropriate in the presence of acid catalysts and if appropriate in the presence of diluents, and, if appropriate, the resulting compounds are subjected to an addition reaction with physiologically acceptable acids.

Surprisingly, the 1,2,3,4-tetrahydro-5-nitro-pyrimidine derivatives of the formula (I) according to the invention are distinguished in a excellent manner by a high effectiveness as insecticides.

The invention preferably relates to compounds of the formula (I) in which
n stands for the numbers 0 or 1,
R stands for the —A—$R^1$ group,
in which
A stands for the —$(CH_2)_m$— or —$(CH_2)_x$—Y—$(CH_2)_z$ groupings,
where
m stands for the numbers 1 to 4,
x and z stand for the numbers 0, 1 or 2, it being possible for x and z to be identical or different, and
Y stands for oxygen, sulphur or for the —NH— or

groupings,
where
$R^2$ stands for optionally $C_1$–$C_4$-alkoxycarbonylsubstituted $C_1$–$C_4$-alkyl, cyano, hydroxyl or for phenyl and
$R^1$ stands for halogeno-$C_1$–$C_4$-alkyl or for radicals from the series comprising phenyl, naphthyl, anthryl, phenanthryl, pyridyl, furyl, thienyl, piperidyl or 1,3-benzodioxlyl which are optionally monosubstituted to pentasubstituted by identical or different substituents, substituents which may be mentioned being: halogen, $C_1$–$C_4$-alkyl, halogeno-$C_1$–$C_2$-alkyl, $C_1$–$C_2$-alkoxy, halogeno$C_1$–$C_2$-alkylthio, hydroxyl, di-$C_1$–$C_2$-alkylamino, carboxyl and phenyl.

Particularly preferred compounds of the formula (I) are those in which
n stands for the numbers 0 or 1,
R stands for the —A—$R^1$ group,
in which
A stands for the —$(CH_2)_m$—or —$(CH_2)_x$—Y—$(CH_2)_z$—groupings,
where
m stands for the numbers 1 to 4, x and z stand for the numbers 0, 1 or 2, it being possible for x and z to be identical or different, and Y stands for oxygen, sulphur or for the —NH— or

groupings,
where

R² stands for optionally alkoxycarbonyl-substituted C₁–C₄-alkyl, cyano, hydroxyl or for phenyl and R¹ stands for halogeno-C₁–C₄-alkyl or for radicals from the series comprising phenyl, naphthyl, anthryl, phenanthryl, pyridyl, furyl, thienyl, piperidyl or 1,3-benzodioxolyl which are optionally monosubstituted to pentasubstituted by identical or different substituents, substituents which may be mentioned being: fluorine, chlorine, bromine, methyl, ethyl, n- or i-propyl, tert.-butyl, trifluoromethyl, methoxy, ethoxy, trifluoromethylthio hydroxyl, dimethylamino, diethylamino, carboxyl and phenyl.

Other preferred compounds according to the invention are addition products of acids and those 1,2,3,4-tetrahydro-5-nitro-pyrimidine derivatives of the formula (I) in which the substituents R, R¹ and R² or the index n have the meanings which have already been preferably mentioned for these substituents and the index.

The acids which can be adducted preferably include hydrohalic acids, such as, for example, hydrochloric acid and hydrobromic acid, in particular hydrochloric acid, furthermore phosphoric acid, sulphuric acid, nitric acid, acetic acid, oxalic acid, malonic acid, succinic acid, maleic acid, tartaric acid, malic acid, fumaric acid, methanesulphonic acid, benzoic acid, substituted benzoic acids, formic acid, chloroacetic acid, toluenesulphonic acid, benzenesulphonic acid, perchloroacetic acid, phthalic acid, naphthalenesulphonic acid, nicotinic acid, citric acid and ascorbic acid.

If, for example, 3-(2-chloro-1,3-thiadiazol-5-ylmethyl)-2-nitromethylene-imidazolidine, 4-fluorobenzylamine and at least twice the molar amount of formaldehyde are used as starting substances in the process according to the invention, the corresponding reaction may be represented by the following equation:

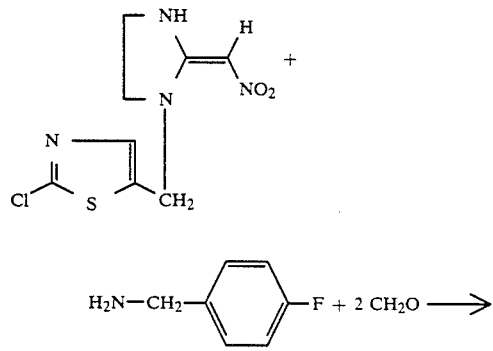

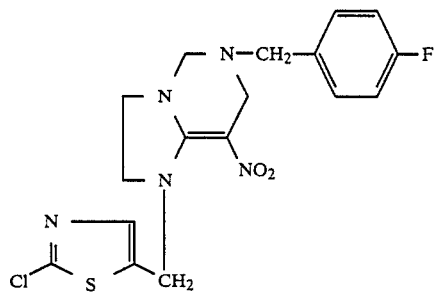

Formula (II) provides a general definition of the nitromethylene derivatives to be used as starting substances in the process according to the invention. In this formula (II), the index n preferably has the meaning which has already preferably been mentioned in connection with the description of the substances of the formula (I) according to the invention for this index n.

The compounds of the formula (II) are known and/or can be prepared by known methods (cf., for example, DE-OS (German Published Specification) No. 2,514,402, EP-OS 136,636, EP-OS 154,178 and EP-OS 163,855).

Formula (III) provides a general definition of the amines also to be used as starting substances in the process according to the invention. In this formula (III), R¹ and A preferably stand for those radicals which have already been preferably mentioned in connection with the description of the substances of the formula (I) according to the invention for these substituents.

The amines of the formula (III) are generally known compounds of organic chemistry.

Examples of compounds of the formula (III) which may be mentioned are:

TABLE 1

| A | R¹ |
|---|---|
| CH₃<br>\|<br>—CH— | (9-anthryl) |
| CH₃<br>\|<br>—CH— | (phenanthryl) |
| CH₃<br>\|<br>—CH— | (phenanthryl) |

TABLE 1-continued

| A | R¹ |
|---|---|
| —CH(CH₃)— | 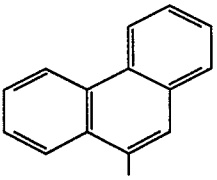 (phenanthrenyl) |
| —CH₂— | 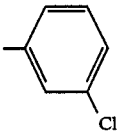 (3-chlorophenyl) |
| —CH₂— |  (4-bromophenyl) |
| —CH₂— | 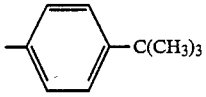 (4-tert-butylphenyl) |
| —CH₂— | 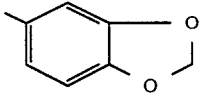 (3,4-methylenedioxyphenyl) |
| —CH₂— | 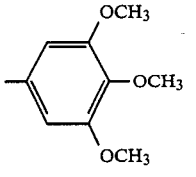 (3,4,5-trimethoxyphenyl) |
| —CH₂— | 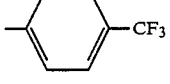 (4-trifluoromethylphenyl) |
| —CH₂— | 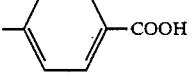 (4-carboxyphenyl) |
| —CH₂— | 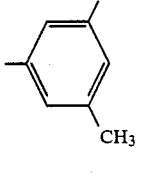 (3,5-dimethylphenyl) |
| —CH₂— | 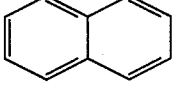 (1-naphthyl) |
| —CH₂—CH₂— | 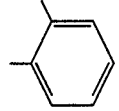 (2-methoxyphenyl) |
| —CH₂—CH₂— | 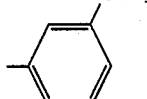 (3-methoxyphenyl) |
| —CH₂—CH₂— | 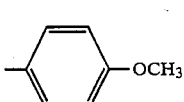 (4-methoxyphenyl) |
| —CH₂—CH₂— | 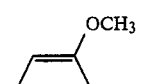 (3,4-dimethoxyphenyl) |
| —CH₂—CH₂— |  (4-hydroxyphenyl) |
| —CH₂—CH₂— | 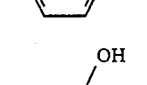 (3,4-dihydroxyphenyl) |
| —CH₂—CH₂— | 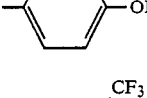 (3-trifluoromethylphenyl) |
| —CH(OH)—CH₂— | 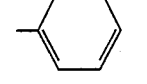 (phenyl) |
| —(CH₂)₃— | 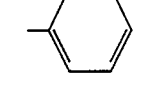 (phenyl) |
| —CH(CH₃)—(CH₂)₂— | 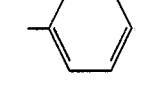 (phenyl) |
| —(CH₂)₄— | 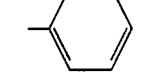 (phenyl) |
| —(CH₂)₂—CH(C₆H₅)— | 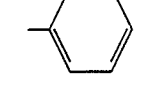 (phenyl) |
| —CH(C₆H₅)—CH₂— | 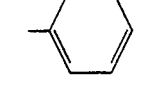 (4-methylphenyl) |

TABLE 1-continued

| A | R¹ |
|---|---|
| —CH(CH₃)— | 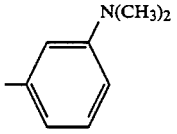 (3-N(CH₃)₂-phenyl) |
| —CH(C₆H₅)—CH₂— | 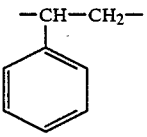 (piperidin-1-yl) |
| —CH(CN)— | 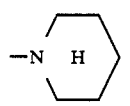 (pentafluorophenyl) |
| —CH(CN)— | 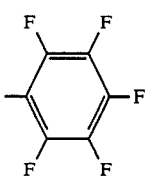 (3-SCF₃-phenyl) |
| \CH—C₂H₅ / | 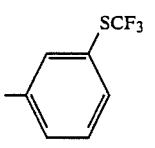 (phenyl) |
| \CH—CH₂—C(=O)—OC₂H₅ / | 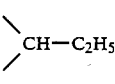 (4-Cl-phenyl) |
| \CH—CH₂—C(=O)—OC₂H₅ / | 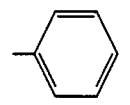 (3,4,5-trimethylphenyl) |
| —CH(CH₃)— | 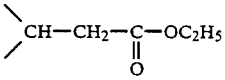 (2,4,6-triisopropylphenyl) |

The process according to the invention for the preparation of the new compounds of the formula (I) is preferably carried out using diluents. Suitable diluents here are water and organic solvents which are inert in the reaction. These preferably include aliphatic and aromatic optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl, dibutyl, glycol dimethyl and diglycol dimethyl ether, tetrahydrofuran and dioxane, and alcohols, such as methanol, ethanol, n-propanol and isopropanol. Mixtures of alcohols and water are preferably employed.

If appropriate, the process according to the invention is carried out in the presence of acidic, non-oxidizing catalysts. Hydrohalic acids, such as hydrochloric and hydrobromic acid, phosphoric acid and lower carboxylic acids, such as acetic acid and propionic acid, have proved particularly suitable.

When carrying out the process according to the invention, the reaction temperatures may be varied within a relatively wide range. In general, the process is carried out at temperatures of between −20° C. and +120° C., preferably at temperatures of between 0° C. and +80° C.

In general, the process according to the invention is carried out under atmospheric pressure. However, the process can also be carried out under increased or reduced pressure.

For carrying out the process according to the invention, 1 to 1.5 moles, preferably 1 to 1.2 moles, of amine of the formula (III) and 2 to 4 moles, preferably 2 to 3 moles, of formaldehyde are employed per mole of nitromethylene derivative of the formula (II).

If appropriate, the amines of the formula (III) can be employed in the form of aqueous solutions. When gaseous amines of the formula (III) are used, these compounds can be passed through the mixture of diluents, compounds of the formula (II) and formaldehyde. In the process according to the invention, formaldehyde is employed as an aqueous solution. In general, the reactions are carried out in a suitable diluent, and the reaction mixture is stirred for several hours at the temperature required in the specific case. In the process according to the invention, working up is carried out in each case by customary methods.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off, and, if appropriate, purified by washing using an inert organic solvent.

The active compounds are suitable for combating animal pests, in particular insects and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, Oniscus asellus, Armadillidium vulgare and Porcellio scaber. From the order of the Diplopoda, for example, Blaniulus guttulatus. From the order of the Chilopoda, for example, Geophilus carpophagus and Scutigera spec. From the order of The Symphyla, for example, Scutigerella immaculata. From the order of the Thysanura, for example, Lepisma saccharina. From the order of the Collembola, for example, Onychiurus armatus. From the order of the Orthoptera, for example, Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria. From the order of the Dermaptera, for example, Forficula auricularia. From the order of the Isoptera, for example, Reticulitermes spp. From the order of the Anoplura, for example, Phylloxera vastatrix, Pemphigus spp., Pediculus humanus corporis, Haematopinus spp. and Linognathus spp. From the order of the Mallophaga, for example, Trichodectes spp. and Damalinea spp. From the order of the Thysanoptera, for example, Hercinothrips femoralis and Thrips tabaci. From the order of the Heteroptera, for example, Eurygaster spp., Dysdercus intermedius, Piesma quadrata, Cimex lectularius, Rhodnius prolixus and Triatoma spp. From the order of the Homoptera, for example, Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp. From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana. From the order of the Coleoptera, for example, Anobium punctatum, Rhizopertha dominica, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica. From the order of the Hymenoptera, for example, Diprion spp., Hoplocampa spp., Lasius spp., Monomorium pharaonis and Vespa spp. From the order of the Diptera, for example, Aedes spp., Anopheles spp., Culex spp., Drosophila melanogaster, Musca spp.. Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa. From the order of the Siphonaptera, for example, Xenopsylla cheopis and Ceratophyllus spp. From the order of the Arachnida, for example, Scorpio maurus and Latrodectus mactans.

The active compounds of the formula (I) according to the invention are distinguished by an excellent insecticidal activity. In particular when applied as leaf insecticides and soil insecticides, they show an excellent action against grubs, such as, for example, Phorbia antiqua grubs, against caterpillars, such as, for example, Plutella maculipennis, against beetle larvae, such as, for example, Phaedon cochleariae and Diabrotica balteata, and aphids, such as, for example, Myzus persicae and Aphis fabae.

Thus, the new compounds are particularly suitable for application in order to combat leaf insects and soil insects.

Furthermore, the new compounds show a bactericidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbon as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can very within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks etc. in the sectors of animal keeping and cattle breeding; better results, for example higher milk production, greater weight, more attractive animal pelt, longer life etc., can be achieved by combating the pests. When applied as ectoparasiticides, in particular, they show an excellent action against blowfly larvae, such as, for example, lucilia cuprina.

The application of the active compounds according to the invention occur in this sector in a known fashion, such as by external application in the form of, for example, dipping, spraying, pouring on, spotting on and dusting.

The biological activity of the compounds according to the invention will be explained with reference to the examples below.

PREPARATION EXAMPLE

Example 1

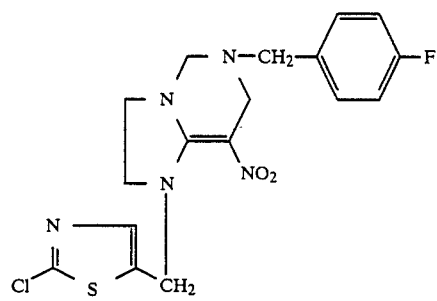

1.5 ml (0.02 mol) of 37% strength aqueous formaldehyde solution are added dropwise and at room temperature to a mixture of 2.6 g (0.01 mol) of 3-(2-chloro-1,3-thiadiazol-5-yl-methyl)-2-nitromethylene-imidazolidine and 1.25 (0.01 mol) of 4-fluorobenzylamine in 90 ml of ethanol, and the mixture is refluxed for 3 hours. The mixture is cooled to room temperature, the solvent is removed in vacuo and ether is added to the residue and filtered off with suction.

3.4 g (83% of theory) of 6,7-dihydro-6-(4-fluorobenzyl)-8-nitro-(5H)-3-(2-chloro-1,3-thiadiazol-5-yl-methyl)imidazolidino-[2,3-f]-pyrimidine of melting point 178° C. are obtained.

The compounds of the formula (I) listed in Table 2 below can be prepared in analogy to Example 1 or the process according to the invention.

TABLE 2

| Example No. | n | R | m.p. °C. |
|---|---|---|---|
| 2 | 1 | —CH$_2$—⟨C$_6$H$_4$⟩—F | 167 |
| 3 | 1 | —CH$_2$—⟨C$_6$H$_4$⟩—Cl (2-Cl) | 117 |
| 4 | 0 | —CH$_2$—⟨C$_6$H$_4$⟩—Cl (2-Cl) | 156 |

TABLE 2-continued

Structure (I):

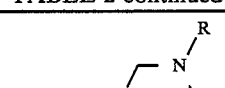

| Example No. | n | R | m.p. °C. |
|---|---|---|---|
| 5 | 0 | —CH₂—(2,4-dichlorophenyl) | 162 |
| 6 | 1 | —CH₂—(2,4-dichlorophenyl) | 98 |
| 7 | 1 | —CH(CH₃)—(4-bromophenyl) (R/S) | 154 |
| 8 | 1 | —CH(CH₃)—(4-methylphenyl) (R/S) | 139 |
| 9 | 1 | —CH(CH₃)—(3,4-dichlorophenyl) (R/S) | yellow viscous oil |
| 10 | 1 | —CH(CH₃)—(3-trifluoromethylphenyl) (R/S) | 91 |
| 11 | 1 | —CH(CH₃)—(2,4,5-trimethylphenyl) (R/S) | 157 |
| 12 | 1 | —CH(CH₃)—(2,4-dichlorophenyl) (R/S) | 94 |
| 13 | 0 | —CH(CH₃)—(2-methoxyphenyl) (R/S) | 157 |
| 14 | 0 | —CH₂—(2-thienyl) | 141 |
| 15 | 0 | —CH₂—(2-furyl) | 119 |
| 16 | 0 | —CH₂—(3-methoxyphenyl) | 139 |
| 17 | 0 | —CH₂—CH(phenyl)₂ | 194 |
| 18 | 0 | —CH(CH₃)—(4-methylphenyl) | 109 |
| 19 | 0 | —CH(phenyl)—CH₂—phenyl | 164 |
| 20 | 0 | —CH(CH₃)—(2-naphthyl) R(+) | 94 |
| 21 | 1 | —CH(CH₃)—(2-naphthyl) R(+) | 78 |

TABLE 2-continued

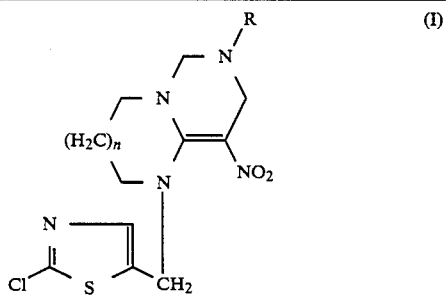

| Example No. | n | R | m.p. °C. |
|---|---|---|---|
| 22 | 1 | —CH₂CH₂—S—CH₂—(2,6-dichlorophenyl) | 91 |
| 23 | 1 | —CH(CH₃)—(2-fluorophenyl) (±) | 142 |
| 24 | 1 | —CH(CH₃)—(3-methoxyphenyl) (±) | 88 |
| 25 | 1 | —CH(CH₃)—(4-biphenyl) | 76 |
| 26 | 1 | —CH(CH₃)—(4-chlorophenyl) | 167 |
| 27 | 1 | —CH(CH₃)—(2-naphthyl) S(−) | 81 |
| 28 | 0 | —CH(CH₃)—(2-naphthyl) S(−) | 89 |
| 29 | 0 | —CH₂—CF₃ | 113 |
| 30 | 0 | —CH(CH₃)—(3-methoxyphenyl) (±) | 150 |

TABLE 2-continued

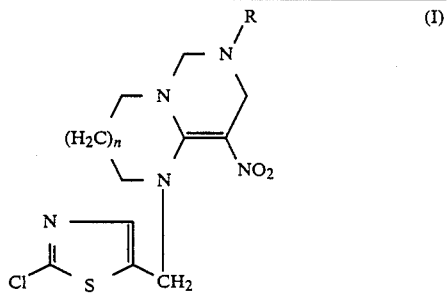

| Example No. | n | R | m.p. °C. |
|---|---|---|---|
| 31 | 0 | —CH₂CH₂—S—CH₂—(2,6-dichlorophenyl) | 139 |
| 32 | 0 | —CH(CH₃)—(2-naphthyl) (±) | 173 |
| 33 | 0 | —CH(CH₃)—(3-bromophenyl) | 154 |
| 34 | 0 | —CH(CH₃)—(3-trifluoromethylphenyl) | 112 |
| 35 | 0 | —CH(CH₃)—(4-biphenyl) (±) | 153 |
| 36 | 0 | —CH(CH₃)—(2-fluorophenyl) (±) | 197 |
| 37 | 1 | —CH₂—(2,6-difluorophenyl) | 171 |
| 38 | 0 | —CH₂—(2,4-difluorophenyl) | 159 |

TABLE 2-continued

Structure (I): Piperazine-type ring with R-N, (H2C)n bridge, =C-NO2, connected to N=C(Cl)-S-C(=CH2)- group.

| Example No. | n | R | m.p. °C. |
|---|---|---|---|
| 39 | 0 | —CH₂CH₂—(2-Cl-phenyl) | 147 |
| 40 | 1 | —CH₂CH₂—(2-Cl-phenyl) | 91 |
| 41 | 0 | —CH₂CH₂—(4-Cl-phenyl) | 131 |
| 42 | 0 | —CH₂—(3,4-diOCH₃-phenyl) | 145 |
| 43 | 1 | —CH₂—(3,4-diOCH₃-phenyl) | 177 |
| 44 | 0 | —CH₂—(4-OCH₃-phenyl) | 152 |
| 45 | 1 | —CH₂—(4-OCH₃-phenyl) | 140 |
| 46 | 0 | —CH₂—(2,5-diF-phenyl) | 162 |
| 47 | 1 | —CH₂—(2,5-diF-phenyl) | 126 |
| 48 | 1 | —CH₂—(3,4-diF-phenyl) | 158 |
| 49 | 0 | —CH₂—(3,4-diF-phenyl) | 160 |
| 50 | 1 | —CH₂—(2-pyridyl) | 127 |
| 51 | 0 | —CH₂—(3-pyridyl) | 58 |
| 52 | 1 | —CH₂—(3-pyridyl) | 137 |
| 53 | 0 | —CH₂—(2-pyridyl) | 149 |
| 54 | 0 | —CH₂—phenyl | 159 |
| 55 | 1 | —CH₂—phenyl | 126 |
| 56 | 1 | —CH₂—(6-Cl-3-pyridyl) | 134 |
| 57 | 0 | —CH₂—(6-Cl-3-pyridyl) | 126 |

TABLE 2-continued

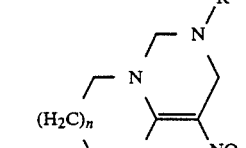

(I)

| Example No. | n | R | m.p. °C. |
|---|---|---|---|
| 58 | 1 | —CH$_2$—C$_6$H$_4$—CH$_3$ (4-methylbenzyl) | 147 |
| 59 | 1 | —CH$_2$—C$_6$H$_4$—F (3-fluorobenzyl) | 119 |
| 60 | 0 | —CH$_2$—C$_6$H$_4$—F (3-fluorobenzyl) | 115 |
| 61 | 0 | —CH$_2$—C$_6$H$_4$—CH$_3$ (3-methylbenzyl) | 127 |
| 62 | 1 | —CH$_2$—C$_6$H$_4$—OCH$_3$ (2-methoxybenzyl) | 133 |
| 63 | 0 | —CH$_2$—C$_6$H$_4$—OCH$_3$ (2-methoxybenzyl) | 161 |
| 64 | 1 | —CH$_2$—C$_6$H$_4$—Cl (4-chlorobenzyl) | 141 |
| 65 | 0 | —CH$_2$—C$_6$H$_4$—Cl (4-chlorobenzyl) | 181 |
| 66 | 0 | —CH(CH$_3$)—C$_6$H$_5$ (R/S) | 169 |
| 67 | 1 | —CH(CH$_3$)—C$_6$H$_5$ R(+) | 177 |
| 68 | 1 | —CH(CH$_3$)—C$_6$H$_5$ S(−) | 161 |
| 69 | 1 | —CH(CH$_3$)—C$_6$H$_5$ (R/S) | 149 |
| 70 | 0 | —CH$_2$CH$_2$—O—CH$_2$—CF$_3$ | 89 |
| 71 | 0 | —CH$_2$—C$_6$H$_3$(2,4-F$_2$) | 152 |
| 72 | 0 | —CH(CH$_3$)—C$_6$H$_4$—Br (R/S) | 78 |
| 73 | 0 | —CH(CH$_3$)—C$_6$H$_2$(CH$_3$)$_3$ (R/S) | 183 |
| 74 | 1 | —CH(C$_6$H$_5$)—CH$_2$—C$_6$H$_5$ | 121 |
| 75 | 1 | —CH$_2$—CH(C$_6$H$_5$)—C$_6$H$_5$ | 196 |

TABLE 2-continued (I)

| Example No. | n | R | m.p. °C. |
|---|---|---|---|
| 76 | 1 | —CH(CH₃)— (R/S), 3-Br-phenyl | 131 |
| 77 | 1 | —CH₂CH₂—(4-Cl-phenyl) | 161 |
| 78 | 1 | —CH(CH₃)— (R/S), 2-naphthyl | 79 |
| 79 | 1 | —CH₂—(2-F-phenyl) | 91 |
| 80 | 0 | —CH₂—phenyl | 167 |
| 81 | 0 | —CH₂—(4-CH₃-phenyl) | 149 |
| 82 | 1 | —CH₂—(3,4-diCl-phenyl) | 167 |
| 83 | 0 | —CH₂—(3,4-diCl-phenyl) | 147 |
| 84 | 0 | —CH(CH₃)—(4-Br-phenyl) | 114 |
| 85 | 0 | —CH(CH₃)—(4-Cl-phenyl) (−) | 113 |
| 86 | 1 | —CH₂—(2,4-diF-phenyl) | 109 |
| 87 | 1 | —CH₂—(2-furyl) | 136 |
| 88 | 1 | —CH(CH₃)—(4-F-phenyl) (±) | 106 |
| 89 | 1 | —CH₂—(2,6-diCl-phenyl) | 158 |
| 90 | 1 | —CH₂—(3-CH₃-phenyl) | 134 |
| 91 | 1 | —CH₂—(3-OCH₃-phenyl) | 171 |
| 92 | 1 | —CH₂—(2-thienyl) | 83 |
| 93 | 0 | 4-F-phenyl | 148 |

TABLE 2-continued

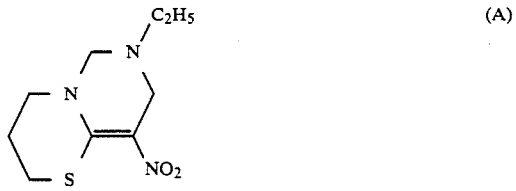

| Example No. | n | R | m.p. °C. |
|---|---|---|---|
| 94 | 0 | phenyl | 177 |

Use Examples

In the following use examples, the following compound was employed as a comparison substance:

(A)

7-Ethyl-9-nitro-3,4,7,8-tetrahydro-(2H,6H)-pyrimidino-[4,3-b]-1,3-thiazine of U.S. patent specification No. 4,031,087.

Example A

Phaedon larvae test
Solvent: 3 parts by weight of dimethyl formamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with mustard beetle larvae (Phaedon cochleariae), as long as the leaves are still moist.

After the desired period of time, the destruction in % is determined. 100% means that all the beetle larvae have been killed; 0% means that none of the beetle larvae have been killed.

In this test, for example the compounds of Preparation Examples 80, 79, 67, 69, 2, 1, 3, 4, 5, 6, 82, 81, 65, 64, 62, 63, 61, 60, 59, 58, 57, 56, 54, 55, 53, 50, 51, 52, 49, 48, 47, 44, 45, 41, 42, 43, 39, 40, 38, 37, 35, 34, 33, 32, 29, 30, 31, 28, 27, 26, 23, 24, 25, 20, 21, 13, 76, 77, 78, 7, 8, 9, 10, 11, 12, 74, 73, 71, 72, 70, 86, 87, 85, and 84 show superior activity compared with the prior art.

Example B

Aphis test (systemic action)
Solvent: 3 parts by weight of dimethyl formamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Vicia faba) which have been heavily infested with the black bean aphid (Aphis fabae) are each watered with 20 ml of the preparation of active compound of the desired concentration in such a way that the preparation of active compound penetrates into the soil without wetting the shoot. The active compound is taken up by the roots and passed to the shoot.

After the desired period of time, the destruction in % is determined. 100% means that all the aphids have been killed; 0% means that none of the aphids have been killed.

In this test, for example the compounds of Preparation Examples 80, 66, 3, 4, 62, 63, 60, 49, 44, 41, 42, 39, 34, 33, 29, 13, 76, 7, 8, 10, 11, 74 and 73 show superior activity compared with the prior art.

Example C

Critical concentration test / root-systemic action
Test insect: Myzus persicae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root-systemic action of the active compound is deduced from the mortality figures. It is 100% if all test insects have been killed and 0% if just as many test insects are still alive as in the case of the untreated control.

In this test, for example the compounds of Preparation Examples 63 and 39 show superior action compared with the prior art.

Example D

Critical concentration test/soil insects
Test insect: Phorbia antiqua grubs (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example the compound of Preparation Example 63 shows superior activity compared with the prior art.

We Claim:

1. A 1,2,3,4-tetrahydro-5-nitropyrimidine derivative of the formula

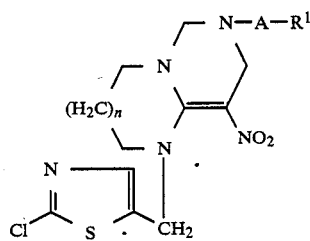

in which
n is 0 or 1,
A is a direct bond, —(CH$_2$)$_m$— or —(CH$_2$)$_x$—Y—(CH$_2$)$_z$,
m is a number from 1 to 4,
x and z each independently is 0, 1 or 2,
Y is oxygen, sulphur, —NH— or

$R^2$ is optionally alkoxycarbonyl-substituted $C_1$–$C_4$-alkyl, or cyano, hydroxyl or phenyl, and
$R^1$ halogeno-$C_1$–$C_4$-alkyl or an optionally substituted radical from the group consisting of phenyl, naphthyl, anthryl, phenanthryl, pyridyl, furyl, thienyl, piperidyl and 1,3-benzodioxolyl each of which is optionally substituted by identical or different substituents selected from the group consisting of fluorine, chlorine, bromine, methyl, ethyl, n- or i-propyl, tert.-butyl, trifluoromethyl, methoxy, ethoxy, trifluoromethylthio, hydroxyl, diethylamino, carboxyl and phenyl,
or an acid addition salt thereof.

2. A 1,2,3,4-tetrahydro-5-nitro-pyrimidine derivative or salt thereof according to claim 1, in which
A is —(CH$_2$)$_m$ or —(CH$_2$)$_x$—Y—(CH$_2$)$_z$, and
$R^2$ is optionally $C_1$–$C_4$-alkoxycarbonylsubstituted $C_1$–$C_4$-alkyl, cyano, hydroxyl or phenyl.

3. A compound according to claim 1, wherein such compound is 6,7-dihydro-6-[1-(2-methoxyphenyl)-ethyl]-8-nitro-(5H)-3-(2-chloro-1,3-thiadiazol-5-yl-methyl)-imidazolidino[2,3,-f]-pyrimidine of the formula

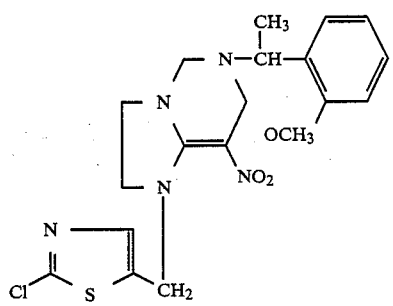

or an acid addition salt thereof.

4. A compound according to claim 1, wherein such compound is 6,7-dihydro-6-(1-biphenyl-ethyl)-8-nitro-(5H)-3-(2-chloro-1,3-thiadiazol-5-yl-methyl)-imidazolidino-[2,3-f]-pyrimidine of the formula

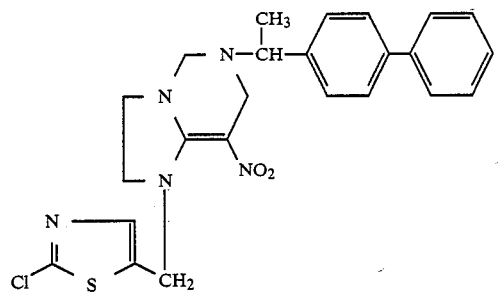

or an acid addition salt thereof.

5. A compound according to claim 1, wherein such compound is 6,7-dihydro-6-(2-methoxy-benzyl)-8-nitro-(5H)-3-(2-chloro-1,3-thiadiazol-5-yl-methyl)-imidazinidino-[2,3-f]-pyrimidine of the formula

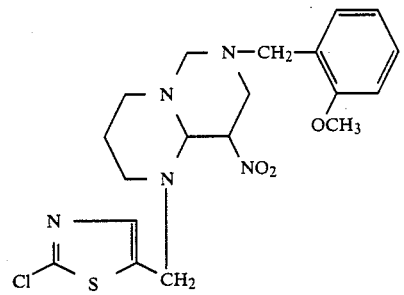

or an addition salt thereof.

6. A compound according to claim 1, wherein such compound is 6,7-dihydro-6-(2-methoxy-benzyl)-8-nitro-(5H)-3-(2-chloro-1,3-thiadiazol-5-yl-methyl)-imidazolidino-[2,3,-f]-pyrimidine of the formula 7. A compound according to claim 1, wherein such compound is 6,7,-dihydro-6-[1-(2,4,5-trimethyl-phenyl)-ethyl]-8-nitro-(5H)-3-(2-chloro-1,3-thiadiazol-5-yl-methyl)-imidazolidino-[2,3-f]-pyrimidine of the formula

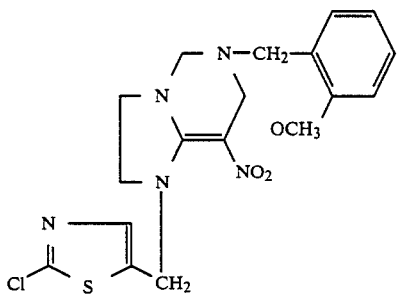

or an addition salt thereof.

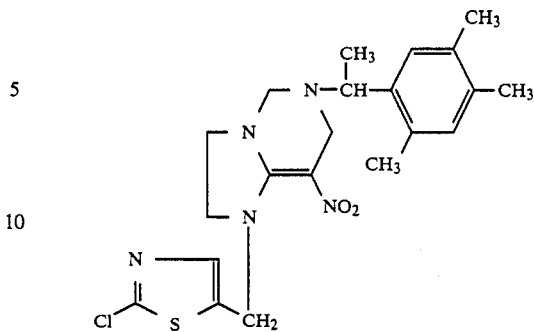

or an addition salt thereof.

8. An insecticidal composition comprising an insecticidally effective amount of a compound or addition salt thereof according to claim 1 and a diluent.

9. A method of combating insects which comprises applying to such insects or to an insect habitat an insecticidally effective amount of a compound or addition salt thereof according to claim 1.

10. The method according to claim 9 wherein such compound is
  6,7-dihydro-6-[1-(2-methoxyphenyl-ethyl]-8-nitro-(5H)-3-(2-chloro-1,3-thiadiazol-5-yl-methyl)-imidazolidino-[2,3-f]-pyrimidine,
  6,7-dihydro-6-(1-biphenyl-ethyl)-8-nitro-(5H)-3-(2-chloro-1,3-thiadiazol-5-yl-methyl)imidazolidino-[2,3-f]-pyrimidine,
  6,7-dihydro-6-(2-methoxy-benzyl)-8-nitro-(5H)-3-(2-chloro-1,3-thiadiazol-5-yl-methyl)imidazinidino-[2,3-f]-pyrimidine,
  6,7-dihydro-6-(2-methoxy-benzyl)-8-nitro-(5H)-3-(2-chloro-1,3-thiadiazol-5-yl-methyl)imidazolidino-[2,3-f]-pyrimidine or
  6,7-dihydro-6-[1-(2,4,5-trimethyl-phenyl)-35hyl]-8-nitro-(5H)-3-(2-chloro-1,3-thiadiazol-5-yl-methyl)-imidazolidino-[2,3-f]-pyrimidine,
or an acid addition salt thereof.

* * * * *

UNITED STATES PATENT AND TRADEMARK OFFICE
CERTIFICATE OF CORRECTION

PATENT NO. : 4,895,850

DATED : January 23, 1990

INVENTOR(S) : Gesing et al

It is certified that error appears in the above-identified patent and that said Letters Patent is hereby corrected as shown below:

| | |
|---|---|
| Col. 25, claim 1 line 37 | Delete " $-(CH_2)_z$, " and substitute -- $-(CH_2)_z$, -- |
| Col. 25, claim 1 line 50 | Delete " $R^1$ halogeno " and substitute -- $R^1$ is halogeno -- |
| Col. 25, claim 2 line 63 | Delete " $-(CH_2)_2$, " and substitute -- $-(CH_2)_2$, -- |
| Col. 25, claim 2 line 64 | Delete " $C_1-C_4$-alkoxycarbonylsubstituted " and substitute -- $C_1C_4$- alkoxycarbonyl-substituted -- |
| Col. 28, claim 8 line 18 | Delete " addition salt " and substitute -- acid addition salt -- |
| Col. 28, claim 9 lines 22-23 | Delete " addition salt " and substitute -- acid addition salt -- |

Signed and Sealed this

Twenty-first Day of April, 1992

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,895,850

DATED : January 23, 1990

INVENTOR(S) : Gesing et al.

It is certified that error appears in the above-identified patent and that said Letters Patent is hereby corrected as shown below:

Col. 28, line 38   Delete " 35hyl " and substitute -- ethyl --

Signed and Sealed this

Sixth Day of July, 1993

Attest:

MICHAEL K. KIRK

Attesting Officer

Acting Commissioner of Patents and Trademarks